US006455016B1

(12) United States Patent
Tsuneki

(10) Patent No.: US 6,455,016 B1
(45) Date of Patent: Sep. 24, 2002

(54) REACTION APPARATUS FOR PRODUCTION OF ALKANOLAMINE

(75) Inventor: Hideaki Tsuneki, Tokyo (JP)

(73) Assignee: Nippon Shokubai Co. Ltd., Osaka (JP)

( * ) Notice: Subject to any disclaimer, the term of this patent is extended or adjusted under 35 U.S.C. 154(b) by 0 days.

(21) Appl. No.: 09/545,722

(22) Filed: Apr. 7, 2000

(30) Foreign Application Priority Data

| Apr. 9, 1999 | (JP) | 11-102975 |
| Apr. 12, 1999 | (JP) | 11-104582 |
| Jun. 10, 1999 | (JP) | 11-163920 |

(51) Int. Cl.[7] ............ B01F 1/00; B01F 3/08; B01J 8/02; F28D 21/00
(52) U.S. Cl. ............ 422/224; 422/190; 422/198; 422/224
(58) Field of Search ............ 422/189, 198, 422/211, 224, 188, 190; 564/463, 477

(56) References Cited

U.S. PATENT DOCUMENTS

| 3,595,626 A | 7/1971 | Sowards | 23/283 |
| 3,697,598 A | * 10/1972 | Weibull et al. | 564/477 |
| 3,986,839 A | 10/1976 | Queiser et al. | 23/288 R |
| 4,400,539 A | 8/1983 | Gibson et al. | 564/480 |
| 4,438,281 A | 3/1984 | Johnson, Jr. | 564/477 |
| 4,847,418 A | 7/1989 | Gibson et al. | 564/477 |
| 4,939,301 A | 7/1990 | Grice et al. | 564/477 |
| 5,795,550 A | 8/1998 | Minami | 422/219 |
| 6,063,965 A | 5/2000 | Nygaard et al. | 564/477 |

FOREIGN PATENT DOCUMENTS

| DE | 298636 A5 | 5/1992 |
| EP | 0 652 207 A1 | 5/1995 |
| GB | 1 529 193 | 10/1978 |
| JP | 5-285367 | 11/1993 |
| JP | 10-66858 | 3/1998 |
| SE | 158 167 | 3/1957 |

OTHER PUBLICATIONS

Grimshaw et al., "Ion–exchange: Introduction to Theory and Practice", The Chemical Society Monographs for Teachers No. 29, including a translation. ©1975.

Ohkubo, "Development of Catalyst Packing Technique for Hydrogenated Refine Reaction Tower in Static Bed", Petrotech 20:76–81, 1997, including a partial translation.

Vamling et al., "Comparison of Some Solid Catalysts for the Production of Ethanolamines from Ammonia and Ethylene Oxide in the Liquid Phase", Ind. Eng. Chem. Prod. Res. Dev. 25:424–430, 1986.

* cited by examiner

Primary Examiner—Jerry D. Johnson
Assistant Examiner—Alexa A. Doroshenk
(74) Attorney, Agent, or Firm—Fish & Richardson P.C.

(57) ABSTRACT

Selective production of a dialkanolamine is attained by controlling the volume preceding the entrance to a catalyst bed and the temperature prevailing under respectively fixed levels subsequent. to the mixture of an alkylene oxide thereby repressing a reaction occurring in the absence of a catalyst and curbing the formation of trialkanolamine. The reactant fluid is prevented from generating a channeling by disposing an exportable structure in a reactor thereby creating the state of a false shell-and-tube type reactor. The reaction is initiated with the inlet temperature set at a higher level than the prescribed level and the alkylene oxide concentration set at a lower level than the prescribed level and thereafter the inlet temperature and the alkylene oxide concentration are gradually changed toward the respectively prescribed levels.

3 Claims, 7 Drawing Sheets

REACTION APPARATUS FOR PRODUCTION OF ALKANOLAMINE

BACKGROUND OF THE INVENTION

1. Field of the Invention

This invention relates to a reaction apparatus to be used in the production of an alkanolamine, a method for production of an alkanolamine using the apparatus, a reactor, a method for charging the reactor with a catalyst, and a method for start-up of the production of an alkanolamine.

More specifically, it relates to a reaction apparatus to be used in producing a dialkanolamine by the reaction of ammonia, a monoalkanolamine, and an alkylene oxide in the presence of a solid catalyst, a method for selectively producing the dialkanolamine using the reaction apparatus, a reactor to be used in the production of an alkanolamine, a method for charging the reactor with a catalyst, and a start-up method for safe and efficient production of an alkanolamine using an adiabatic reactor in the presence of a solid catalyst by adjusting the temperature and the concentration of the raw material components during the contact between the raw materials and the catalyst.

2. Description of the Related Art

As a commercial approach to the production of an alkanolamine by the amination of an alkylene oxide with ammonia, the method which produces ethanolamine by the reaction of ethylene oxide with aqua ammonia (ammonia concentration in the range of 20–40 wt. %) has been in vogue. Though this method forms three species of amine, i.e. monoethanolamine, diethanolamine, and triethanolamine, it is required to repress the formation of triethanolamine among other species of amine because the demand for triethanolamine is decreased. The reaction, therefore, is generally carried out with the molar ratio of ammonia and ethylene oxide set at a large ammonia excess in the approximate range of 3–5. In spite of the effort, the selectivity of triethanolamine is in the range of 10–20 wt. % or more and the selectivity of diethanolamine is not more than 40% by weight.

In an anhydrous system, substantially no reaction occurs between an alkylene oxide and ammonia. For the reaction of this nature, therefore, a catalyst is indispensable. Thus, homogeneous catalysts such as organic acids, inorganic acids, and ammonium salts have been proposed (Swedish Patent No. 158,167). These homogeneous catalysts are difficult to be separated from the reaction system and fail to manifest fully satisfactory performance.

As an embodiment of the immobilization of such a homogeneous acid catalyst, an ion-exchange resin having a sulfonate group immobilized on resin has been proposed (U.S. Pat. No. 3,697,598). Since this catalyst manifests relatively good activity and selectivity, it has been already practiced on a commercial scale. The ion-exchange resin, however, entails the problem of having a low maximum working temperature. The ion-exchange resins which are commercially available generally have rather low maximum working temperatures of 120° C. ("Ion Exchange— Introduction to Theory and Practice" translated jointly by Rokuro Kuroda and Masami Shibukawa, published by Maruzen Co., Ltd., 1981, page 34). When ammonia and ethylene oxide are subjected to a reaction at a lowered molar ratio, the temperature of the catalyst bed is eventually compelled by the heat of reaction to exceed the heat resistant temperature. When the catalyst is used under these temperature conditions for a long time, it entails the problem of inducing deterioration of the catalyst. It is, therefore, difficult to lower the molar ratio of ammonia and ethylene oxide to a level in the approximate range of 20–25. With a view to overcoming the drawback of poor high-temperature resistance of the ion-exchange resin, an inorganic catalyst excelling in thermal stability has been studied.

U.S. Pat. No. 4,438,281 discloses silica alumina in popular use manifests a good catalytic activity.

Industrial and Engineering Chemistry, Product Research and Development, 1986, Vol. 25, pp. 424–430 publishes a comparative study performed between ion-exchange resins and various kinds of zeolite catalysts, etc. Particularly, in terms of the selectivity to a monoalkanolamine, no other substances used in this study surpassed ion-exchange resins.

U.S. Pat. No. 4,939,301 discloses acid activated clay catalysts. Some of these catalysts have manifested high yields of monoethanolamine of not less than 60% by weight. Since no catalyst has manifested a fully satisfactory selectivity to a monoalkanolamine, the reaction of ammonia and ethylene oxide is carried out with the molar ratio of these reactants increased to not less than 20–30 times the stoichiometric level. This reaction, however, is hardly practicable because the cost of equipment for recovering ammonia for cyclic use is prohibitive.

With a view to solving these problems, EP 652 207 A proposes use of a catalyst having a rare earth element carried on a heat-resistant carrier to produce a monoalkanolamine with a high selectivity. Since this catalyst is aimed at producing a monoalkanolamine with a high degree of selectivity, it is still deficient to produce a dialkanolamine.

A catalyst having a high degree of selectivity for a dialkanolamine can be obtained by using a microporous material having an effective pore diameter in the range of 0.45 to 0.8 nm or a catalyst obtained by subjecting this microporous material to an ion-exchange treatment and/or a surface treatment.

When the dialkanolamine further obtained by the use of this catalyst with a still higher degree of selectivity, the amount of the dialkanolamine ought to be increased theoretically by separating the monoalkanolamine formed in advance and recycling part of the separated monoalkanolamine to the reaction system. Neither an apparatus nor a method available for this method has been specifically disclosed, this method has a problem yet to be solved for the purpose of production to practice.

It has been known to produce an alkanolamine by the reaction of liquid ammonia with an alkylene oxide as disclosed in for example U.S. Pat. No. 3,697,598 and EP 652 207 A.

This production, when carried out on a commercial scale, however, has the possibility of inducing a channeling of the reaction mixture in the catalyst bed or an outflow of fine catalyst particles from the reactor.

For the purpose of preventing this channeling in a relatively large reactor, it needs to use a special catalyst packing device or a reactor of a complicated shape as described for example in JP-A-10-66,858, JP-A-07-60,102, JP-A-05-285, 367, and PETROTECH, Vol. 20, pp. 960–965.

In recent years, with a view to overcoming the problem of heat resistance due to the use of such an ion-exchange resin, the feasibility of using an inorganic catalyst which excels in thermal stability under adiabatic conditions has been studied. EP 652 207 A for example, discloses catalyst for the production of an alkalolamine, which are characterized by carrying a rare earth element on a heat resisitant inorganic carrier. Since this catalyst itself carries heat resistance unlike an ion-exchange resin, the reaction can be carried out at a temperature of 50–300° C., preferably of 80–200° C. By using such a heterogeneous catalyst excelling in heat resistance, it is possible to increase the ratio of the alkylene oxide, improve the productivity of the reaction, and repress the ratio of ammonia to a low level, and thereby miniaturizing the reactor. Further, since the reaction temperature can be maintained at a high level, the efficiency of the reaction can be improved. In addition, the adiabatic reaction has an advantage that, when the reaction starts once, it continues the reaction by heat generated and ensures the sufficient rise of temperature necessary for performing the reaction promptly.

When the reaction of ammonia with an alkylene oxide is effected with the heterogeneous catalyst excelling in heat resistance under the adiabatic conditions between the exterior and the reactor, the interior of the reactor assumes an unstable state for a short while after the start-up. When the heterogeneous catalyst excelling in heat resistance is used, the ethylene oxide concentration can be maintained at a rather high level and the corresponding alkanolamine can be produced efficiently because the ratio of the ethylene oxide to ammonia can be increased. When the conditions remain in a stable state as described above, the alkanolamine can be produced in a constant quality because the reaction temperatures in the pre-heater and the reactor are stable and the molar ratio of the ethylene oxide to ammonia is stable as well.

In contrast, during the initial stage of the reaction which precedes to these stable conditions, the rapid production of the alkanolamine is difficult. Since the reaction is initiated at the time that the contact is established between the raw material components and the catalyst, the internal temperature of the reactor does not immediately rise uniformly after the introduction of the mixed liquid of raw materials, i.e. ammonia and the alkylene oxide, into the reactor with the catalyst. The internal temperature of the reactor does not rise to the highest reaction temperature till the mixed gas reaches the terminal end of the catalyst bed and thus the internal temperature has its distribution varied from the inlet toward the outlet, of the reactor. When the heterogeneous catalyst excelling in heat resistance is used particularly, the difference in temperature between the inlet and the outlet of the reactor is increased because the rise of temperature is large. When the temperature of the inlet of the reactor which is in a steady state is adopted at the time of start-up, not only the raw material substances are wasted because the alkylene oxide fails to react and the unaltered alkylene oxide copiously flows out of the reactor during the initial stage of the reaction but also the reaction possibly raises the problem of safety because the reactive alkylene oxide enters the ammonia recovery system. Further, if the product includes the unaltered raw materials in a large amount, it becomes difficult to produce the product homogeneously. The control of reaction temperature is difficult because the temperature of the catalyst is not stable. The rapid rise of the temperature during the start-up possibly entails dangers such as polymerization of a monomer component and blockage of the catalyst bed.

The mere increase of the ratio of ammonia to the ethylene oxide, however, brings such disadvantages as lowering the efficiency of the reaction and expanding the size of the reactor proportionate to the increase in the amount of ammonia as well.

When the catalyst such as the conventional ion-exchange resin which is deficient in heat resistance is used, the reaction temperature is low. This low reaction temperature is obtained by increasing the molar ratio of ammonia to the ethylene oxide to a level of not less than about 25. Under these conditions, even the adiabatic reaction brings only a small rise of temperature in the reactor. Thus, even when no special operation is made during the start-up or when the temperature in the catalyst bed is not uniform, neither any special inconvenience nor any noticeable hindrance is suffered to arise. The development of the heterogeneous catalyst excelling in heat resistance and reactivity, however, has forced the start-up preceding the stable state to encounter the problems mentioned above.

SUMMARY OF THE INVENTION

Even in a system without a catalyst, an alkylene oxide reacts with a monoalkanolamine or a dialkanolamine at a relatively large reaction rate. The reaction rate is nearly equal between the two species of amine or rather larger with the dialkanolamine. No selectivity exists for the formation of dialkanolamine. When the monoethanolamine is recycled with the object of obtaining the dialkanolamine by the reaction of ammonia with an alkylene oxide, the reaction of the alkylene oxide with the monoalkanolamine occurs before the arrival at the catalyst bed and consequently forms not only the dialkanolamine but also the trialkanolamine, with the problematic result that the selectivity of the dialkanolamine will be lowered and, at the same time, the amount of the triethanolamine will be increased.

As a result of a diligent study with a view to solving the problem, it has been found that the use of a reaction apparatus so constructed as to allow the mixing of the ammonia with a monoalkanolamine to preheat and supplying an alkylene oxide into the preheated fluid can suppress the by-production of triethanolamine. Consequently, the present invention has been achieved. The by-production of the triethanolamine can be further suppressed by the use of a reactor whose available volume from the feed inlet of the alkylene oxide to the entrance of the catalyst bed is not more than 0.5 times the volume of the catalyst bed in the reactor.

An object of the present invention is to provide a method for producing a dialkanolamine with a high degree of selectivity and an apparatus therefor.

The object mentioned above is accomplished by a reaction apparatus for producing a dialkanolamine with a high selectivity by causing ammonia and amonoalkanolamine to react with an alkylene oxide in the presence of a solid catalyst, which reaction apparatus is provided with a mixer for mixing ammonia with a monoalkanolamine, a pre-heater for preheating the fluid flowing from the mixer, an alkylene oxide mixer with a feed inlet for supplying an alkylene oxide and interposed between the pre-heater and a reactor for supplying an alkylene oxide via the feed inlet and mixing it into a fluid preheated by the pre-heater, and a reactor adapted to introduce the preheated mixture of ammonia, monoalkanolamine, and alkylene oxide flowing from the alkylene oxide mixer and with a catalyst bed packed with a solid catalyst.

The object mentioned above is further accomplished, in the production of a dialkanolamine with a high selectivity by the reaction of ammonia with a monoalkanolamine and an alkylene oxide in the presence of a solid catalyst, by a method for the production of a dialkanolamine which is characterized by supplying the alkylene oxide to a fluid obtained by mixing ammonia with a monoalkanolamine and preheating the resultant mixture.

The reaction apparatus of this invention is capable of repressing the conversion of a dialkanolamine into the trialkanolamine and allaying the degradation of the selectivity of the dialkanolamine.

The method of this invention is capable of repressing the conversion of a dialkanolamine into the trialkanolamine and allowing a dialkanolamine to be produced conveniently and efficiently.

The object of the present invention is, in view of the situation described above, to provide a reaction apparatus which prevents the solution from generating a channeling in the catalyst bed and prevents particles of the catalyst from flowing out of the reactor by a simple apparatus and a simple operation and a method for packing a catalyst.

The object mentioned above is also accomplished by a reactor for the production of an alkanolamine, which is characterized by having a honeycomb structure disposed inside the reactor.

Further, the object mentioned above is accomplished by a method for packing a reactor for the production of an alkanolamine with a catalyst, which method is characterized by disposing a honeycomb structure inside a reactor and packing the structure with a catalyst.

The object mentioned above is further accomplished by a method for packing an up-flow type reactor for the production of an alkanolamine with a catalyst, which method is characterized by packing a catalyst having a particle diameter of not more than 1 mm, superposing on the resultant catalyst layer inert particles having a particle diameter of 0.5 to 10 times that of the catalyst, and further superposing on the resultant superposed layer of the inert particles having a particle diameter of 1.5 to 10 times that of the inert particles.

By this invention, the following effects are attained.

1. Generally, in the reactor having a large diameter such as not less than 1 m, the resistance to flow path is smaller in the part of the catalyst bed lying along the lateral wall of the reactor than that among the catalysts. As a result, the raw materials in the reactor inevitably induce the phenomenon of flowing with deviation from the central part to the lateral wall side, of the reactor (column) i.e. the so-called channeling. This phenomenon is caused by the fact that the percentage of voids increases on the wall of the reactor and the fact that the catalyst is tightly packed in the central part.

In the so-called shell-and-tube type reactor, the pressure loss is substantially fixed and the channeling does not occur frequently when the catalyst beds are given a fixed length. While the heat-exchanger type reactor may well do by adopting a shell-and-tube type reactor, the adiabatic reactor cannot be adopted by reason of an inevitable high cost.

The use of the honeycomb structure contemplated by this invention permits formation of a state simulated to that of a shell-and-tube type reactor without appreciably changing the expense of the equipment.

2. The up-flow type reactor requires a catalyst retainer that prevents the catalyst from moving or flowing out. When the catalyst has a relatively large particle diameter, it can be retained with a metallic gauze. When the catalyst having very fine particles is used, the use of a metallic fine mesh gauze has the possibility that the catalyst will block the gauze.

When the inert particles are superposed on the catalyst bed and they have the same particle diameter as the catalyst, then the superposed layer of the inert particles does not function fully satisfactorily as a retaining means. When the inert particles to be used have an ample size for the purpose of retaining the catalyst, the catalyst leaks through the gaps between the adjacent inert particles and these individual retaining particles have an unduly large weight capable of harming the catalyst. This inconvenience can be avoided by superposing inert particles of gradually increased particle diameters.

3. The method for packing the reactor with the catalyst is relatively simple because the reactor can be packed with the catalyst after the honeycomb structure has been disposed in the reactor. Further, the honeycomb structure is a one-piece entity and can be easily disposed in the reactor. Since gaps are formed rarely between the honeycomb structure and the reactor, the fluid handled during the course of the reaction leaks or forms a short pass only rarely.

A further object of this invention is to provide a start-up method that is capable of initiating the production of an alkanolamine safely and efficiently.

The object mentioned above is accomplished by a startup method for the production of an alkanolamine by the reaction of ammonia with an alkylene oxide using an adiabatic reactor in the presence of a solid catalyst, which start-up method is characterized by initiating the reaction at an inlet temperature of the reactor higher than the prescribed temperature at an alkylene oxide concentration lower than the prescribed concentration and subsequently changing the inlet temperature and the alkylene oxide concentration gradually to the prescribed levels, respectively.

When the start-up method according to this invention is carried out, the temperature of the catalyst bed can be maintained at a high level from the beginning of the start-up operation by supplying ammonia at a temperature higher than the prescribed temperature to the reactor (the curve of 17 minutes in the diagram of FIG. 8 to be described below). When the reactor is externally heated, it requires a separate apparatus. In the present invention, however, the inlet temperature of the reactor can be readily heightened by using an adiabatic reactor with a pre-heater that is normally disposed in any apparatus of this class (FIG. 8 to be described below). In this respect, in the operation which produced the results depicted in FIG. 9, the degree of conversion of ethylene oxide was low and the unaltered ethylene oxide flowed out of the reactor because the temperature of the catalyst was not raised fully during the initial stage of reaction and the temperature of the reactor barely began to rise after the elapse of 30 minutes.

Since the alkylene oxide of a rather low concentration is supplied and this concentration is subsequently elevated gradually after the temperature of the reactor has been raised, the alklene oxide so supplied can acquire the reactivity at a sufficiently high catalyst temperature and no unaltered alkylene oxide occur at the outlet of the catalyst bed. Thus, the product of high quality can be obtained with high efficiency because it is not necessary to remove unaltered raw materials from the product. The favorable outcome of this operation maybe logically explained by a supposition that, as clearly noted from FIG. 10 which will be described below, the start-up can be stably implemented even under such conditions that the molar ratio of the alkanolamine to ammonia may be as low as 8 and the ethylene oxide concentration may be high.

According to the start-up method of this nature, the elevation of temperature cannot occur rapidly because the temperature of the catalyst bed is gradually elevated by the heat of reaction. Even when the steady operation is carried out at a high alkylene oxide concentration by the use of a heterogeneous catalyst excelling in heat resistance, the possibility of this operation entailing polymerization of a monomer component and blockage of a catalyst bed due to an abrupt change of temperature during the course of the startup operation is nil.

The above and other objects, features and advantages of the present invention will become clear from the following description of the preferred embodiments.

DETAILED DESCRIPTION OF THE PREFERRED EMBODIMENT(S)

Figure 1:
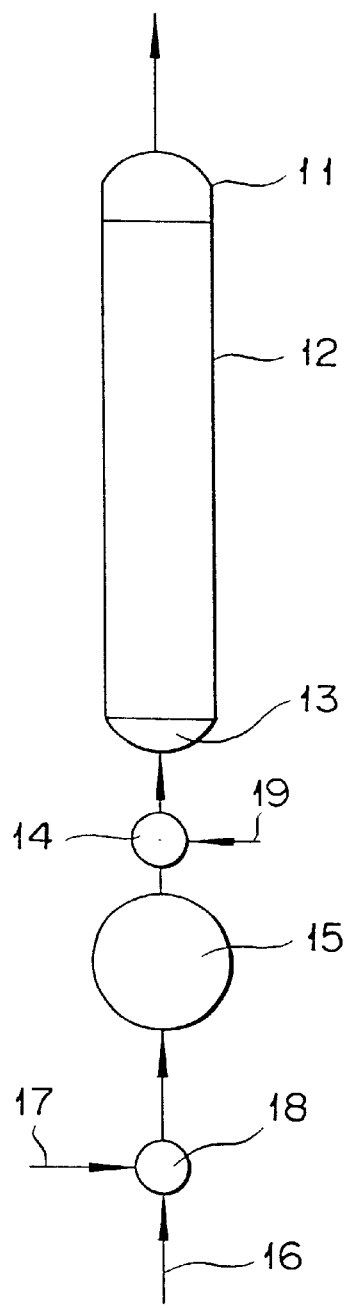
FIG. 1 is an illustration of the reaction apparatus of Example I-1.

The alkylene oxide to be used in this invention, though not specifically limited, is preferably a compound of 2–4 carbon atoms represented by the following structural formula 1:

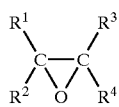

(1)

wherein $R^1$, $R^2$, $R^3$, and $R^4$ independently represent a hydrogen atom, a methyl group, or an ethyl group. As concrete examples of the compound, ethylene oxide, propylene oxide, and butylene oxide may be cited. This invention may use these alkylene oxides either singly or a combination of two or more species. For this invention, ethylene oxide proves advantageous among other alkylene oxides because it allows the production of ethanolamines particularly useful economically.

The solid catalyst for use in this invention is not particularly limited but has only to be adapted for the production of alkanolamines. As concrete examples of the solid catalyst, it may cite known ion-exchange resins used for the production of alkanolamines; zeolites; catalysts having compounds of rare earth elements such as lanthanum, cerium, praseodymium, neodymium, samarium, europium, gadolinium, terbium, dysprosium, holmium, erbium, thulium, ytterbium, ruthenium, scandium, and yttrium carried on refractory inorganic carriers having a specific surface area of 1–500 $m^2/g$ such as, natural substances (such as diatomaceous earth, pumice, and clay), simple oxides (such as silica, alumina, titania, and zirconia), complex oxides (such as silica-alumina, titania-silica, zirconia-silica, and perovskite), refractory inorganic substances (such as silicon carbide, silicon nitride, and graphite), and inorganic ion exchangers (such as SAPO, MeAPO, metallosilicate, layered clay compounds, ion-exchange resins, and zeolites) and products obtained by forming or molding compounds of the rare earth elements in combination with the heat-resistant carriers mentioned above.

The term "particle diameter" as used herein means the average diameter of catalysts and inert particles. It is not applied exclusively to spheres but maybe applied to arbitrary shapes such as cylinders, fragments, and rings as well. Spheres and approximate spheres prove particularly advantageous for inert particles among other shapes in terms of the ease of handling. The particle diameter (equivalent diameter) of such a catalyst is required not more than 1 mm, preferably in the range of 1–0.1 mm. If the particle diameter exceeds the upper limit of the range, it will lower the amount of the product to be obtained. If it falls short of the lower limit of the range, it will entail a disadvantage in suffering the catalyst to flow out of position or increasing the pressure loss.

The "adiabatic reactor" or briefly the "reactor" for use in this invention is not particularly limited but only required a continuous-flow type reactor which is capable of continuing a given reaction in an adiabatic state. The term "adiabatic state" as used herein refers to the condition in which the transfer of heat between the reactor and the exterior thereof is blocked. The reactor that has the perimeter thereof coated with an insulating material, for example, answers this description. This invention is aimed at providing a method for effecting efficient production of an alkanolamine by effectively utilizing the heat of reaction generated by the contact of the catalyst with the raw material components and further controlling the temperature of reaction by adjusting the concentration of the raw material components. The adiabatic reactor that is externally provided with a cooling device and consequently enabled to adjust the reaction temperature at a fixed level and the adiabatic reactor which is furnished with an external heater and consequently enabled to fix the internal temperature of the reactor primarily do not belong to the adiabatic reactor that is contemplated by the present invention. The adiabatic reactor that is furnished with such a temperature adjusting device, however, may be used for implementing the method of this invention. This performance of the method, when effected without using the temperature adjusting device, equals the operation of the adiabatic reactor of this invention.

By varying the molar ratio of ammonia and the alkylene oxide, it is possible to produce three kinds of product (monoalkanolamine, dialkanolamine, and trialkanolamine) having 1, 2, and 3 alkylene oxide molecules added to one ammonia molecule. As concrete examples of the alkanolamine, it may cite (mono-, di-, and tri-) ethanolamines, (mono-, di-, and tri-) propanolamines, and (mono-, di-, and tri-) butanolamines.

In the first—third modes of embodiment to be cited herein below, the alkylene oxide as raw material, catalyst, reactor, and alkanolamine described above will be used unless otherwise specified.

Now, this invention will be described below with reference to the first mode of embodiment of the invention.

This invention relates to a reaction apparatus for use in the production of a dialkanolamine mainly by the reaction of ammonia, amonoalkanolamine, and an alkylene oxide in the presence of a solid catalyst, which apparatus is characterized by being so constructed as to supply the alkylene oxide to a fluid which has been formed by mixing ammonia and the monoalkanolamine and then preheating the resultant mixture. The reaction apparatus mentioned above is provided with a mixer for mixing ammonia with a monoalkanolamine; a pre-heater for preheating the fluid flowing from the mixer; an alkylene oxide mixer with a feed inlet for supplying an alkylene oxide and interposed between the pre-heater mentioned above and a reactor for introducing an alkylene oxide via the feed inlet and mixing it into a fluid preheated by the pre-heater; and a reactor adapted to introduce the preheated mixture of the ammonia, monoalkanolamine, and alkylene oxide flowing from the alkylene oxide mixer and possessed of a catalyst bed packed with a solid catalyst.

The mixer for mixing ammonia and a monoalkanolamine is not particularly limited but required only to be capable of mixing the ammonia and monoalkanolamine. A method of joining a pipe for ammonia to a pipe for monoalkanolamine in the pattern of the letter T or the letter Y may be cited as one concrete example of the concept of the mixer.

The pre-heater for preheating the fluid flowing from the mixer is not particularly limited but required only to be capable of preheating the mixed fluid composed of ammonia and a monoalkanolamine. Heat exchangers, particularly pre-heaters, may be cited as concrete examples of the pre-heater. The heat exchangers include, for example, shell-and-tube type heat exchangers, double-pipe type heat exchangers, single-pipe type heat exchangers, and plate-type heat exchangers. The shell-and-tube type heat exchangers prove particularly advantageous from the viewpoint of the efficiency of heat exchange.

The alkylene oxide mixer provided with a supply inlet for an alkylene oxide, interposed between the pre-heater mentioned above and the reactor, and adapted to introduce the alkylene oxide through the supply inlet into the fluid preheated by the pre-heater mentioned above is not particularly limited but required only to be capable of mixing the preheated fluid and anlkylene oxide. A method for joining a pipe for the preheated mixture to a pipe for alkylene oxide in the pattern of the letter T or the letter of Y and a method for effecting the mixture by the use of a nozzle may be cited as concrete examples of the alkylene oxide mixer. The structure molded like the letter T and provided with a nozzle proves particularly favorable from the viewpoint of the efficiency of mixing.

The reactor adapted to introduce the preheated mixture of ammonia, monoalkanolamine, and alkylene oxide flowed from the alkylene oxide mixer and furnished with a catalyst bed packed with a solid catalyst is not particularly limited but required only to be capable of implementing adiabatic reaction because the reaction involved herein is adiabatic reaction. As concrete examples of this reactor, it may cite fixed-bed type reactors and cascade fixed-bed reactors. The fixed bed type reactors prove particularly favorable among other reactors cited above from the viewpoint of the cost of equipment.

In the reaction apparatus for use in this invention, the available volume from the supply inlet for an alkylene oxide through the inlet of the catalyst bed is expected generally not more than 0.5 times, more preferably in the range of 0.01 to 0.5 times, and especially 0.01 to 0.2 times, the volume of the catalyst bed which is formed in the reactor. The term "available volume" as used herein refers to the volume from the supply inlet for the alkylene oxide to the mixed fluid of ammonia and monoalkanolamine through the inlet of the catalyst bed in the reactor. It should take care of the size of this volume because the dialkanolamine is converted into the trialkanolamine by a reaction in the absence of a catalyst. If this available volume is unduly large, the reaction will give rise to the corresponding trialkanolamine and the selectivity of dialkanolamine is degraded proportionately. The expression "volume of the catalyst bed" refers not only to the catalyst alone but also to the apparent volume of the catalyst, inclusive of the voids entrained. Specifically, the formation of trialkanolamine by the reaction in the absence of a catalyst must be repressed for the purpose of allaying the decline of the degree of selectivity of dialkanolamine. This repression of the reaction in the absence of a catalyst can be attained by decreasing to the fullest possible extent the dead volume extending to the catalyst bed.

Further, the reaction apparatus of this invention is preferably provided with a static mixer (mixer using no agitation) between the alkylene oxide mixer and the reactor. The incorporation of such a static mixer results in exalting the efficiency of mixing a fluid.

The reaction apparatus of this invention is preferably packed with a liquid-pervious inert material on the upstream side in the interior of the reactor. The liquid-pervious inert material to be used herein is not particularly limited but required only to avoid interacting with the reactants. As concrete examples of the liquid-pervious inert material, it may cite a casting, crush, woolen material of quartz, α-alumina, stainless steel, carbonized silicon, and silica. By the incorporation of such a liquid-pervious inert material, it is possible to preheat the fluid effectively and enhance readily the efficiency of the reaction.

This invention concerns a method for the production of a dialkanolamine by the reaction of ammonia, a monoalkanolamine, and an alkylene oxide in the presence of a solid catalyst, which method is characterized by supplying the alkylene oxide to the preheated fluid formed in advance by mixing the ammonia and monoalkanolamine and pre-heating the resultant mixture.

Among other catalysts enumerated above, the molded particles of zeolite which has undergone ion-exchange with a rare earth element, in particular MFI or MEL structure (code exhibiting the structure by International Zeolite Society), proves particularly advantageous from the viewpoint of the selectivity of diethanolamine. Among other rare earth elements, lanthanum, yttrium, and cerium prove particularly advantageous from the viewpoint of the cost of catalyst.

The monoalkanolamine as the raw material for use in this invention is preferred to be a compound represented by the following structural formula 2:

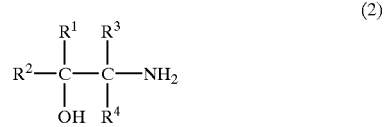

(2)

wherein $R^1$, $R^2$, $R^3$, and $R^4$ have the same meanings as in the structural formula 1. Ethanolamine may be cited as one concrete example of this compound.

The monoalkanolamine formed in the conventional production of an alkanolamine may be separated by a known method such as distillation and part of the separated monoalkanolamine may be used as the raw material for the monoalkanolamine contemplated by this invention.

The dialkanolamine that corresponds to the raw material mentioned above is obtained. It is preferred to be a dialkanolamine that is represented by the following structural formula 3:

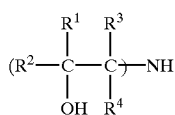

(3)

wherein $R^1, R^2, R^3$, and $R^4$ have the same meanings as in the structural formula 1. Diethanolamine may be cited as one concrete example of this compound.

In the method of this invention, the time required for the preheated fluid which has received the alkylene oxide to reach the catalyst mentioned above is preferred not more than 0.5 times, more preferably in the range of 0.01 to 0.5 times, and especially 0.01 to 0.2 times, the retention time in the catalyst bed. The retention time in the catalyst bed in this case is represented by the formula, (Volume of catalyst bed) (Volumetric flow rate).

Further, in the method of this invention, the temperature of the fluid at the inlet of the catalyst bed is preferred to be lower by not less than 50° C., preferably 50 to 150° C., than the temperature at the outlet of the catalyst bed. Since this reaction is adiabatic, the temperature in the direction of cross section of the catalyst bed may be substantially uniform. By causing the temperature of the fluid at the inlet of the catalyst bed to lower by not less than 50° C., preferably 50 to 150° C., especially 60 to 150° C., than the temperature at the outlet of the catalyst bed, it is possible to lower the formation speed of the trialkanolamine in the site of absence of a catalyst and consequently repress the formation of trialkanolamine. As a result, the decline of the selectivity of the dialkanolamine can be prevented. Specifically, by lowering the temperature at the inlet of the catalyst bed to the minimum, it is possible to lower the reaction rate at the site of the absence of a catalyst and repress the formation of the trialkanolamine.

When this method elects to use the cascade type reactor, the temperature of the fluid at the inlet of the catalyst bed in the second and following stages is preferably cooled to a level lower by not more than 50° C., preferably 50 to 150° C., than the temperature at the outlet of the catalyst bed at the immediately preceding stage. By cooling the fluid at the inlet of the catalyst bed at the second and following stages to not more than 50° C., preferably 50 to 150° C., especially 60 to 150° C., than the temperature at the outlet of the catalyst bed at the immediately preceding stage, it is possible to lower the formation speed of the trialkanolamine at the site the absence of a catalyst, repress the formation of the trialkanolamine, and prevent the decline of selectivity of the dialkanolamine.

The reaction apparatus may be provided with one reactor or a plurality of reactors. The number of reactors may be selected, depending on the degree to which the dialkanolamine aimed at is formed.

Since the reaction of this invention must be carried out in the state of a liquid phase, the reaction pressure is preferably maintained at a level higher than the vapor pressure of the reaction mixture at the highest temperature to be reached in the reactor. In the latter half of the reactor, the elevation of temperature can be curbed by utilizing the latent heat of vaporization obtained by vaporizing part of ammonia. In this case, the reaction pressure is lowered than the vapor pressure of the reaction mixture.

The reaction may be carried out in any of the modes, i.e. down flow, upper flow, and horizontal flow, relative to the catalyst. Generally, the mode of upper flow proves favorable among other modes from the viewpoint of the ease with which the catalyst is packed.

The production of a dialkanolamine is generally carried out at a temperature in the range of 5–300° C., preferably in the range of 20–200° C. The operation pressure is generally in the range of 5–20 MPa, preferably in the range of 7–15 MPa.

The molar ratio of ammonia and a monoalkanolamine is not particularly limited but required only to be such that the amount of a monoalkanolamine in the reaction system may be larger than the amount thereof which is not substantially consumed. It is expected generally in the range of 200:1–1:2, preferably in the range of 100:1–1:1, and more preferably in the range of 50:1–2:1.

The molar ratio of an alkylene oxide and monoalkanolamine is expected generally in the range of 1:0.01–1:20, preferably in the range of 1:0.05–1:10, and more preferably in the range of 1:0.1–1:8. If the proportion of an alkylene oxide is less than 0.01, the amount of diethanolamine is not increased. Conversely, if this proportion exceeds 20, the excess will be at a disadvantage in increasing the recycle of the monoalkanolamine to an excessive extent.

Under the reaction conditions mentioned above, the liquid hourly space velocity (LHSV) is preferred in the range of 0.1–50 hr$^{-1}$ from the viewpoint of the productivity.

Now, this invention will be described below with reference to the second mode of embodiment of the invention.

For the production of an alkanolamine, the fixed-bed type reactor is generally used. In this reactor, one or more one-piece honeycomb structures are disposed. The one-piece honeycomb structure has a catalyst for the production of an alkanolamine packed and retained therein and is put to use for a given reaction. The one-piece structure in the shape of a cylinder, for example, has a plurality of non-crossing through holes from one end face toward the other end face and is manufactured in a known method such as a method of combining sheet elements of prescribed shapes and compressing or rolling them. The size of the honeycomb structure is properly decided, depending on the amount of the product aimed at. The shape of the flow paths for the raw material liquid in the honeycomb structure is not particularly limited but required only to avoid exerting a large load on the fluid. It may be any of various shapes such as circle, hexagon, square, triangle, and corrugation. Since the alkanolamine obtained by the reaction is corrosive, the material for the one-piece honeycomb structure is preferred to have a corrosion-proofing quality. Stainless steel, for example, may be used as the material. The size of the individual flow paths (lattice or cell) has no particular limitation. For the purpose of enhancing the effect of the false shell-and-tube type structure, this size is expected preferably not more than 30 cm and more preferably in the range of 10–2 cm. Further, from the viewpoint of preventing the fluids of the raw materials and the product from forming a channeling, the adjacent through holes of the one-piece structure are preferred to be impervious to liquid.

The reactor may be provided therein with one or more honeycomb structures. When a plurality of honeycomb structures are provided in the reactor, the individual flow paths in the honeycomb structures may be varied in size. It is permissible, for example, to give decreasing diameters to the flow paths on the upstream side of the fluid of raw materials and increasing diameters to the flow paths on the downstream side or vice versa. The plurality of honeycomb structures may be serially arranged in the flow direction of the raw materials. Alternatively, it is permissible to interpose a suitable empty space between the structures in the flow directions of the fluids and mix the fluids by utilizing the empty spaces to enhance the efficiency of agitation.

The one-piece honeycomb structure is preferred such that it may be carried in its unmodified form into the reactor or similarly carried out from the interior of the reactor. When the honeycomb structure is formed in a one-piece construction and the upper part of the reactor is formed in an open-close construction resorting to such a closing device as a flange, then the honeycomb structure can be readily carried into and out of the reactor through the upper part thereof. Consequently, the inner part of the reactor itself is not formed in a complicated construction because the honeycomb structure is formed in a one-piece construction.

Preferably, the reactor is provided in the inner wall of the lower end thereof with a hollow disc for passing the fluid of raw materials so as to ensure fast retention of the honeycomb structure therein and, at the same time, prevent leakage of liquid through the gap between the reactor and the honeycomb structure. Further, the hollow part of the hollow disc is preferably provided with a gauze or a mesh capable of retaining the catalyst which is packed in the honeycomb structure.

The catalyst in a prescribed amount is dropped into the honeycomb structure in the reactor till the structure is packed to capacity with the catalyst.

The reaction is generally a liquid-phase reaction under pressure. The flow of the liquid phase may be in any of the three modes, down-flow, up-flow, and horizontal flow. Generally, the upper flow proves favorable from the viewpoint of the case of packing the catalyst.

In the up-flow type reactor, the upper side of the catalyst bed is overlain by a retainer layer of inert particles having a particle diameter of 0.5 to 10 times that of the catalyst. The superposed layer of the inert particles is further overlain by inert particles having a particle diameter of 1.5 to 10 times that of the former inert particles. Though the ratio of the catalyst, the inert particles having a particle diameter of 0.5 to 10 times, and the finally superposed inert particles having a particle diameter of 1.5 to 10 times is not particularly limited, it is generally in the range of 10–100 1–10: 2–20, preferably in the range of 10–500: 1–5 2–10 (by volume). If the ratio deviates from this range, the superposed layers of inert particles will fail to retain the catalyst bed so fast as to preclude the catalyst bed from flowing or moving randomly. This method of packing the catalyst to the reactor is not limited but may be similarly applied to a reactor of other type.

As concrete examples of the inert particles to be used effectively in this invention, molded masses, fragments, and woolly masses made of granules of quartz, $\alpha$-alumina, stainless steel, silicon carbide, and silica may be cited. The inert particles formed as spheres or approximate spheres prove particularly favorable among other shapes of inert particles in terms of the ease of handling.

When the catalyst needs to be replaced with a new supply, by removing the gauze or the mesh disposed in the hollow part of the hollow disc, the used catalyst may be easily extracted from the honeycomb structure. The packing of the newly supplied catalyst can be effected in the same manner as described above.

Now, this invention will be described below with reference to the third mode of embodiment of the invention.

This invention concerns a start-up method for the production of an alkanolamine by the reaction of ammonia and an alkylene oxide using an adiabatic reactor in the presence of a solid catalyst, which start-up method is characterized by initiating the reaction at a higher inlet temperature of the reactor than the prescribed temperature with a lower alkylene oxide concentration than the prescribed concentration and subsequently gradually changing the inlet temperature and the alkylene dioxide concentration toward the prescribed levels, respectively.

By using the heterogeneous catalyst, it is possible to heighten the molar ratio of an alkylene oxide to ammonia and produce an alkanolamine efficiently. The reaction, however, is so active that the interior of the reactor may become unstable, the control of temperature may become difficult during the course of the start-up, and the product may be contaminated with the unaltered raw material. In accordance with the start-up method of this invention, however, by adjusting the concentration of an alkylene oxide and the temperature of the raw material substances introduced into the reactor, it is possible to preclude the rapid rise of temperature, ensure safety of the reaction, and prevent the possible leakage of the unaltered raw material into the ammonia recovery system.

Now, the present invention will be described in detail below.

Among other heterogeneous catalysts, this invention finds an inorganic catalyst preferable and a catalyst having a rare earth element carried on a heat-resistant carrier particularly preferable on account of excellent heat resistance. Since this invention is aimed at ensuring the safety of the reaction during the course of the start-up when the rise of the temperature in the adiabatic reaction is large, the inorganic catalyst is particularly suitable for effecting this invention because it excels in heat resistance and allows a large temperature rise in the adiabatic reaction. As a result, this invention enables the reaction temperature to be adjusted with the molar ratio of ammonia to the alkylene oxide and, so long as the catalyst excels in heat resistance, also allows the alkylene oxide ratio to be heightened and enables the production of an alkanolamine to be attained with unusually high efficiency.

Further, since this invention is capable of repressing the elevation of temperature in the reactor (continuous-flow type reactor), it allows the ion-exchange resin which, on account of deficiency in heat resistance, has been heretofore rejected as not usable when the molar ratio of ammonia and an alkylene oxide is low (when the concentration of an alkylene oxide is high in the reaction mixture) to be used therein as a heterogeneous catalyst.

The adiabatic reactor used herein may be any of the known adiabatic reactor which is packed with a heterogeneous catalyst and then put to use for producing an alkanolamine from ammonia and an alkylene oxide. The reactor is packed in the interior thereof with the heterogeneous catalyst. The method for supplying the raw material to the reactor and the method for packing the reactor with the catalyst are not particularly limited. By illustrating in FIG. 7 a reaction apparatus as one example of the mode of embodying this invention, the method for producing an alkanolamine by the reaction of ammonia and an alkylene oxide in an adiabatic reactor in the presence of a solid catalyst will be briefly described.

For a start, ammonia from an ammonia cylinder 710 is supplied via an ammonia pump 704 and an alkylene oxide from an alkylene oxide cylinder 711 is supplied via an alkylene oxide pump 705 respectively to a pre-heater 702. The raw materials thus supplied are heated in the pre-heater 702 and introduced into a reactor 701. The temperature in the pre-heater in which the reaction has been stabilized is maintained in a range of 20–100° C., preferably in the range of 30–80° C., and especially in the range of 30–70° C. If this temperature is less than 20° C., it will not maintain the temperature of a catalyst 703 proper for a highly efficient reaction. Conversely, if the temperature exceeds 100° C., it will render the temperature adjustment in the reactor difficult, with the reaction heat generated in the reactor as a contributory factor.

The mixture of raw materials that has been introduced into the pre-heater is guided to the inlet of the reactor, with the temperature thereof kept intact. The alkylene oxide is converted into the corresponding alkanolamine by reacting with ammonia in the reactor 701. Though the internal temperature of the reactor in the steady state is not particularly limited, it is preferably in the range of 20–300° C., more preferably in the range of 30–250° C., and most preferably in the range of 30–200° C. Incidentally, the internal temperature of the reactor largely varies from the inlet toward the outlet of the reactor because the reaction is adiabatic. The temperature mentioned above, therefore, does not mean that the temperature is uniform at this level from the inlet through the outlet of the reactor.

The temperature of the reactor 701 is brought by the temperature of the raw material components heated in the pre-heater coupled with the consequently generated heat of reaction. If the reaction temperature in the adiabatic reactor is lower than 20° C., it will decrease the reaction rate and unduly increase the amount of the catalyst for thorough conversion of the alkylene oxide into the corresponding alkanolamine. If the reactor is enlarged with a view to overcoming such drawback, it will boost the cost of equipment prohibitively. Conversely, if the reaction temperature is higher than 300° C., it will raise the internal temperature of the reactor excessively and possibly color the product. Incidentally, the adjustment of the internal temperature of the reactor can be attained under the adiabatic condition by adjusting the temperature of the pre-heater and the molar ratio of an alkylene oxide and ammonia.

Though the amount of ammonia to be added relative to the alkylene oxide is not particularly limited, it is preferably in the range of 2–30 mols, and more preferably in the range of 4–20 mols, per mol of the alkylene oxide. Thus, the reaction temperature can be adjusted by the molar ratio mentioned above. If this amount is less than 2 mols, it will excessively increase the molar ratio of the alkylene oxide to ammonia, excessively increase the reaction heat to be generated, and possibly cause coloration of the product. Conversely, if the amount exceeds 30 mols, it will excessively decrease the molar ratio of the alkylene oxide to ammonia and excessively increase the amount of ammonia to be recovered.

The reaction pressure in a stabilized state is preferably in the range of 2–30 MPa, more preferably in the range of 4–20 MPa, and especially in the range of 5–15 MPa. If the reaction pressure is lower than 2 MPa, it will not enable the reaction to keep perfectly in the liquid-phase condition, excessively increasing the amount of ammonia to vaporize, and suffering the liquid-phase part to decrease to the extent of preventing the reaction of ammonia and the alkylene oxide from proceeding smoothly. Conversely, if the reaction pressure is higher than 30 MPa, it will require unduly high pressure resistance and boosting the cost of the equipment.

Though the reaction is carried out in the liquid phase, the conditions of temperature and pressure may be so set as to allow vaporization of part of the ammonia during the course of the reaction. In this case, the heat of vaporization of ammonia represses the elevation of temperature in the reactor and permits the reaction to proceed at a high alkylene oxide concentration.

Under the conditions mentioned above, the liquid hourly space velocity (LHSV) is preferably in the range of 0.5–100 $hr^{-1}$ and more preferably in the range of 1–50 $hr^{-1}$, though depending on the reaction temperature and the kind and the amount of the catalyst. If the LHSV is smaller than 0.5 $hr^{-1}$, it will excessively increase the amount of the catalyst for thorough conversion of the alkylene oxide into the corresponding alkanolamine, notwithstanding the contact time between ammonia and the alkylene oxide is elongated and the conversion of the alkylene oxide into the corresponding ankanolamine is attained with high efficiency. Further, the amount of the alkanolamine to be produced per unit time will be decreased. The increase of the reactor in size brings the disadvantage of necessitating a proportionate addition to the cost of equipment. Conversely, if the LHSV is larger than 100 $hr^{-1}$, it will shorten the contact time between ammonia and the alkylene oxide and consequently failing to attain sufficient conversion of the alkylene oxide into the corresponding alkanolamine. Incidentally, the LHSV during the start-up operation may be different from that in the static condition.

Through the top of the reactor, ammonia and the alkanolamine as the product are distilled and introduced into an ammonia recovering column 707, wherein the ammonia and the alkanolamine are separated from each other. The alkanolamine as the product is obtained through the bottom of the ammonia recovering column 707. Meanwhile, the ammonia which has been distilled through the top of the ammonia recovering column is cooled and separated by a heat-exchanger 709 and recovered in an ammonia recovering tank 708. The ammonia thus recovered can be introduced into the pre-heater 702 via a recycle ammonia pump 706.

Now, the start-up method of this invention to be used in initiating the process for the production of the alkanolamine described above will be explained below.

First, the raw materials excluding the alkylene oxide are preheated in the pre-heater 702. The preheating temperature is higher by 20–100° C., preferably by 30–90° C., and especially by 40–80° C., than the prescribed temperature. By heating the ammonia exclusively and feeding the heated ammonia to the reactor, it is possible to equalize the inner temperature of the catalyst bed with that of the fluid of raw materials. Consequently, it is possible to heighten the reaction rate of the alkylene oxide to be supplied subsequently.

The term "prescribed" as used in this invention refers to the steady state in which the reaction is stabilized with the catalyst and the molar ratio of ammonia and alklene oxide maintained under approximately fixed conditions. The term "prescribed temperature" as used herein refers to the temperature of the inlet of the reactor under the steady state mentioned above. Where the raw material compounds are directly introduced from the pre-heater to the reactor, the temperatures of the pre-heater and the inlet of the reactor are equal. Incidentally, the prescribed temperature of the inlet of the reactor is variable with such factors as the kinds of catalyst to be used, the molar ratio of ammonia and an alkylene oxide, and the scale of the reactor. When this method is adopted, the prescribed temperature of the inlet of the reactor is generally in the range of 20–100° C., preferably in the range of 30–90° C., and more preferably in the range of 30–80° C. So long as the prescribed temperature which is set in consideration of the fact that the product succumbs to coloration under the condition of a high temperature falls in the range mentioned above, the rapid rise of temperature can be prevented and, at the same time, the distillation of the unaltered product can be prevented.

Subsequently, an alkylene oxide at a prescribed concentration in the range of 10–90 v/v %, preferably in the range of 20–80 v/v %, and especially in the range of 20–70 v/v % is supplied to the reactor. If the concentration exceeds 90 v/v %, it will be difficult to avoid the rapid elevation of the reaction temperature due to the reaction heat of the alkylene oxide. Conversely, if this concentration is less than 10 v/v %, it will fail to obtain a fully satisfactory heat of reaction. The term "prescribed concentration" as used herein refers to the concentration of the alkylene oxide under the conditions of steady state. It is variable with such factors as the kind of catalyst to be used and the molar ratio of ammonia.

Then, after the reaction has advanced and the temperature of the catalyst bed has begun to be elevated by the heat of reaction, the temperature of the pre-heater 702 is gradually lowered toward the prescribed temperature and the alkylene oxide concentration is gradually increased toward the prescribed alkylene oxide concentration. The adjustment of the preheating temperature, therefore, can be judged by confirming the elevation of the catalyst temperature.

This invention concerns a start-up method for obtaining the product of excellent quality safely under the condition that the reaction heat generated is utilized more efficiently using an adiabatic reactor. In accordance with this invention, by initiating the reaction at a reaction temperature higher than the prescribed temperature, it is possible to prevent the unaltered alkylene oxide from flowing out of the reaction system. Moreover, by initiating the reaction at a lower alkylene oxide concentration than the prescribed concentration, the temperature in the catalyst bed is not suffered to rise excessively and the degradation of quality of the product is not suffered to ensue even when the temperature of the inlet of the reactor is higher than the prescribed temperature. Even by setting the temperature in the catalyst bed once at a slightly higher level than the prescribed temperature and subsequently gradually changing the inlet temperature and the alkylene oxide concentration toward the prescribed levels, respectively, it is possible to preclude rapid change of the temperature of the catalyst bed, stabilize the interior of the reactor, eliminate the possibility of inducing polymerization of a monomer component and clogging of the catalyst bed, and prevent the unaltered alkylene oxide from flowing out of the reaction system The first through third modes of embodiment mentioned above, when necessary, may be suitably combined without departure from the scope of this invention.

EXAMPLES

Now, the present invention will be described below with reference to the accompanying drawings that depict examples of the invention. Example I represents a case of producing diethanolamine by using ethylene oxide mainly as an alkylene oxide solely for the purpose of illustration. It is not meant to limit this invention.

Example I-1

FIG. 1 is an illustration of a reaction apparatus. The apparatus in FIG. 1 was used to carry out a liquid-phase reaction. Ammonia supplied via an ammonia line 16 and a monoalkanolamine recycle via a monoalkanol amine line 17 were mixed in a mixer 18. The resultant mixture (fluid) was heated to a temperature in a pre-heater 15 and then mixed in an alkylene oxide mixer 14 with the alkylene oxide fed via an alkylene oxide line 19. The available volume of a reactor 11 inclusive of the volume of an inlet part 13 was set at not more than 0.5 times the volume of a catalyst (packed) bed 12.

Specifically, the reactor 11 was formed of a stainless steel tube, 20 mm in inside diameter and 200 mm in length, which was wrapped on the perimeter thereof with a warming heater and insulated with an insulating material. The inlet part 13 of the reactor (catalyst bed) was filled with quartz wool spread in a thickness of 10 mm so as to serve concurrently as a retainer for the catalyst. The pre-heater 15 was wrapped on the perimeter thereof with a heater. It was formed of a stainless steel tube, 10 mm in inside diameter and 100 mm in length. The temperature of the pre-heater was controlled with the temperature of the fluid in the middle part of the pre-heater.

The catalyst bed 12 was packed with 10 cm$^3$ of a catalyst obtained by compression molding ZSM-5 zeolite which had been ion-exchanged with lanthanum and crushing the resultant mold to a particle size of 50–100 mesh (based on Japanese Industrial Standard).

Ammonia was fed at a flow rate of 18.8 g/hr and monoethanolamine at a flow rate of 6.7 g/hr as liquid reactants by the use of a high pressure pump to the pre-heater and were heated therein to 70° C. The heated reaction fluid and ethylene oxide added thereto at a flow rate of 3.23 g/hr were together fed into the reactor (LHSV=4.9 hr$^{-1}$). The inlet temperature of the reactor was 60° C. The reaction pressure was controlled constantly at 10 MPa with a control valve disposed at the outlet of the reactor. The temperature of the catalyst bed at the outlet of the reactor was 130° C.

When the product at the outlet of the reactor was analyzed, it was found to comprise 65.8 wt. % of MEA, 32.2 wt. % of diethanolamine (DEA), and 2.0 wt. % of triethanolamine (TEA). The selectivity of DEA exclusive of the recycled MEA was 90 wt. %. For the sake of the evaluation of performance, the degree with which the by-production of TEA was repressed during the production of DEA and the degree of selectivity with which the DEA was produced formed important considerations. The formation ratio of TEA and DEA was used as an index. In the present example, the ratio of TEA/DEA was 0.062. The conditions used and the TEA/DEA ratio are shown in the following Table 1.

Comparative Example I-1

Figure 2:
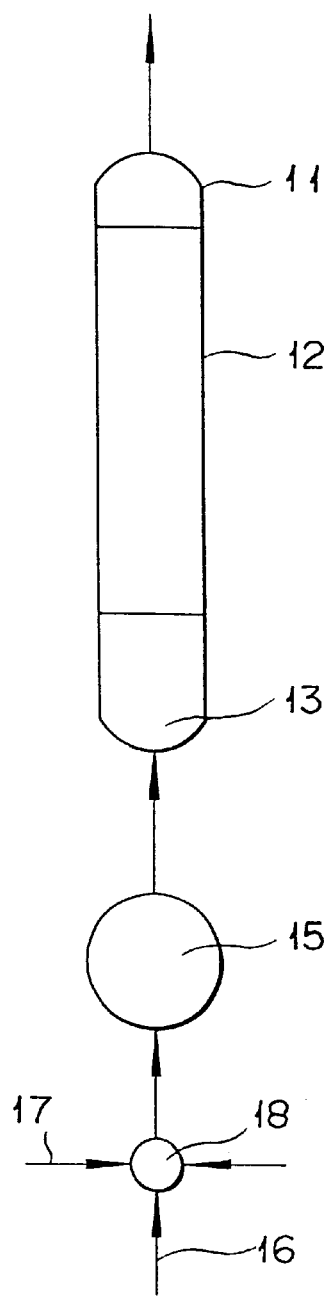
FIG. 2 is an illustration of the reaction apparatus of Comparative Example I-1.

FIG. 2 is an illustration of a reaction apparatus. The apparatus shown in FIG. 2 was used to carry out a reaction. The reference numerals in the diagram are identical with those of FIG. 1.

Though the reactor and the pre-heater used herein were the same as those of Example 1, the ethylene oxide was mixed in front of the pre-heater. The volume of the reactor plus the pre-heater was 8 cm$^3$.

The reaction was carried out by following the procedure of Example I-1. The results are shown in the following Table 1.

Comparative Example I-2

A procedure was performed by following the procedure of Comparative Example I-1 while changing the temperature of the pre-heater to 90° C. and doubling the feed rate of the raw materials. The results are shown in the following Table 1.

The reaction proceeded even in the pre-heater and the temperature at the inlet of the reactor was raised to 98° C. The temperature at the outlet of the reactor was 140° C.

Example I-2

Figure 3:
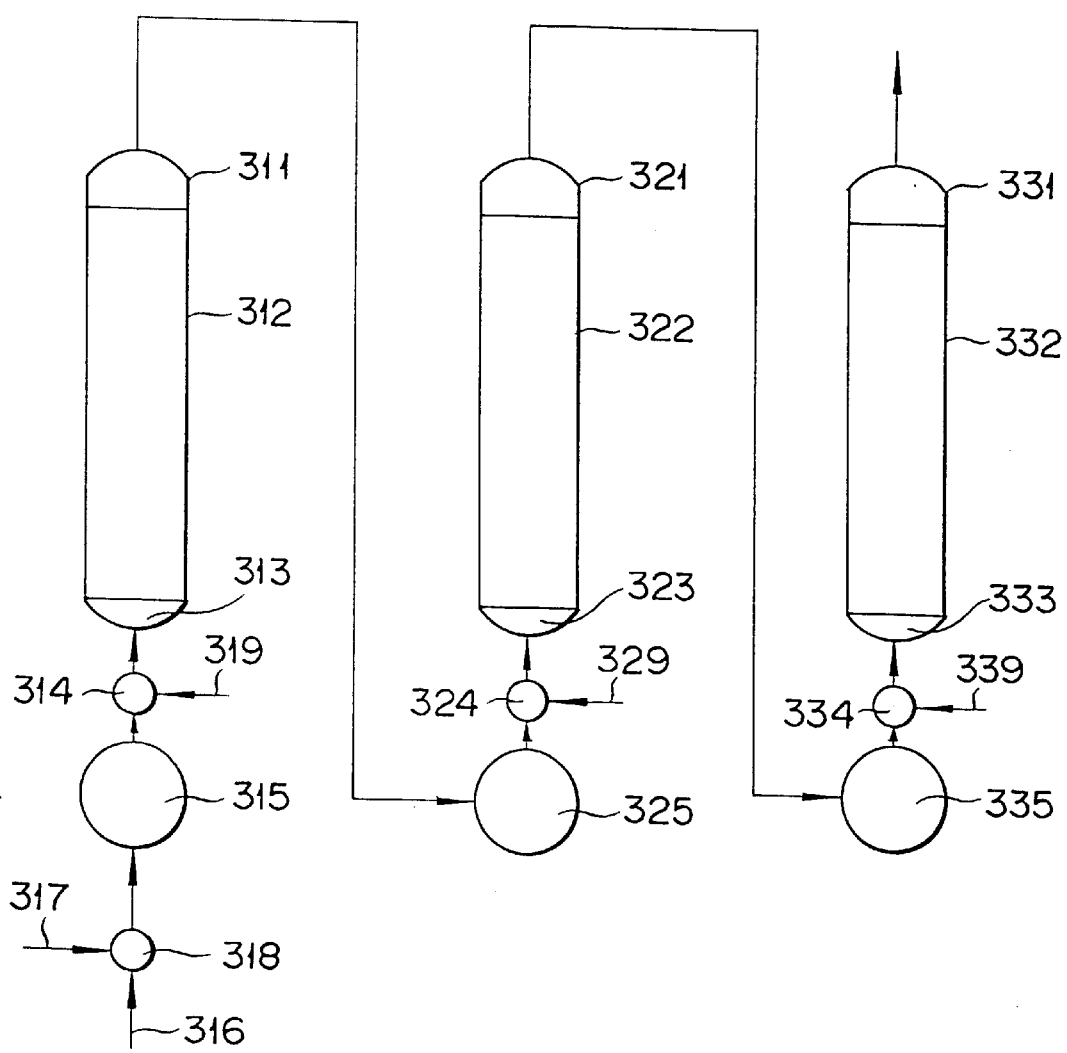
FIG. 3 is an illustration of the reaction apparatus of Example I-2.

FIG. 3 represents an illustration of a reaction apparatus of this example. In FIG. 3, the reference numerals which are the sums of the reference numeral 310 and 10 or 20 represent the same members or parts as those denoted respectively by the reference numerals 310–319. In FIG. 3, ammonia supplied via an ammonia line 316 and a monoalkanolamine supplied via a monoalkanolamine line 317 are mixed in a mixer 318, heated to a prescribed temperature in a pre-heater 315, then mixed with ethylene oxide supplied via a line 319, and supplied to a reactor 311. The fluid at the outlet of reactor was cooled with the heat exchanger 315 to a level lower by not less than 50° C. than the outlet temperature. The cooled fluid and additional ethylene oxide supplied via a line 329 were mixed and the resultant mixture was supplied further to a second reactor 321. Further, the fluid at the outlet of the reactor was cooled with a heat-exchanger 316 to a level lower by not less than 50° C. than the outlet temperature. The cooled fluid and additional ethylene oxide supplied via a line 339 were mixed and the resultant mixture was supplied to a third reactor 331.

TABLE 1

| | Ratio of available volume/catalyst bed | Temperature of pre-hater ° C. | TEA/ DEA |
|---|---|---|---|
| Example 1 | 0.08 | 70 | 0.062 |
| Comparative Example 1 | 0.8 | 70 | 0.077 |
| Comparative Example 2 | 0.8 | 70 | 0.102 |

DEA: Diethanolamine
TEA: Triethanolamine

The following facts are known from Table 1.
(1) Triethanolamine was formed in a larger amount in Comparative Example I-1 than in Example I-1.
(2) Though the productivity in Comparative Example I-2 was improved because the temperature was raised, the TEA was formed in a fairly large amount. This fact may imply that the reaction for converting DEA into TEA in the absence of a catalyst occurred before the reactants reached the catalyst bed in the reactor.

Example II-1

Figure 4:
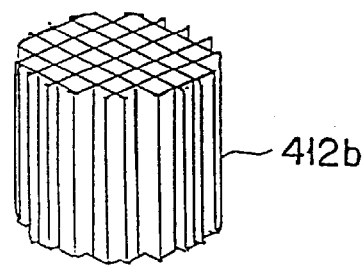
FIG. 4 is an explanatory diagram illustrating a method for assembling the reactor of Example II-1.
Figure 4:
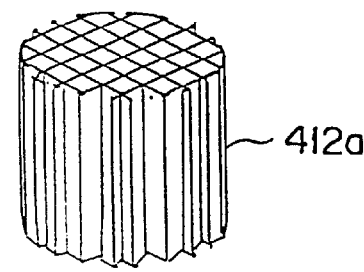
Figure 4:
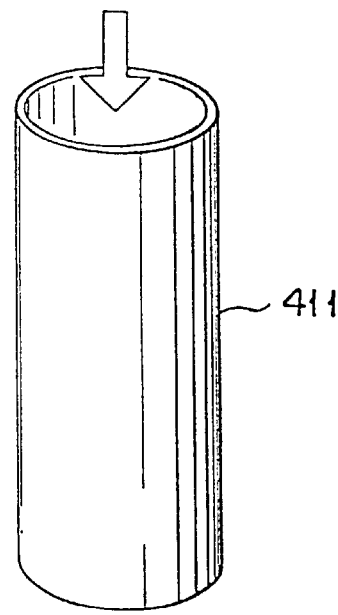

FIG. 4 illustrates the reactor of Example II-1 according to the second mode of embodying this invention and the honeycomb structure disposed in the reactor.

Reference numeral 411 is a reactor proof against pressure. This reactor was furnished at the upper and lower ends thereof with flat panels. In a process for producing an alkanolamine, the reactor 411 had an inner volume only on the order of several cubic meters ($m^3$). Since it was used under such high pressure as 10–15 MPa, it was preferred to assume a slender shape. The diameter of the reactor, therefore, is only on the order of 1 to 4 meters. In this case, the apparatus having a complicated structure is not suitable for filling with a catalyst. It was advantageous in this case to use a reactor with such a structure as illustrated in FIG. 4.

By providing the reactor 411 on the inner wall of the lower end thereof with a hollow disc (not shown), it was possible to prevent the leakage of liquid through the gap between the reactor 411 and the honeycomb structure 412.

Further, the reactor may be provided on the upstream side of the catalyst bed disposed therein with a distributor which was intended to uniform the flow of raw materials up to the catalyst bed.

Two structures 412a and 412b were packed in the reactor. One structure or three structures may be used instead. When the plurality of such structures were installed, the angles of the lattice were preferred to be staggered. The structures were not required to resist pressure because they were installed within the reactor. They were formed by assembling fairly thin plates.

Though the size of the individual through holes (lattice) is not particularly limited, it is preferably not more than 30 cm, more preferably not more than 10 cm for the purpose of enhancing the effect of the false shell-and-tube type reactor.

Example II-2

Figure 5:
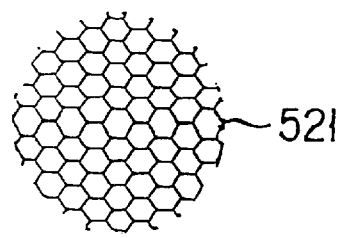
FIG. 5 is a plan view of a structure to be disposed in the reactor of Example II-2.

FIG. 5 is a plan view illustrating a structure 521 of Example II-2 as viewed from above. In the manufacture of the structure combining thin sheets, the use of such a hexagon as shown in the diagram was convenient. Since the lattice formed of squares at times prevented the catalyst from filling the squares uniformly to the corners thereof, the hexagons were advantageous from the viewpoint of ensuring uniform packing of the catalyst.

The size of each cell is preferably not more than 30 cm, more preferably not more than 10 cm in terms of the radius of an inscribed circle.

Example II-3

Figure 6:
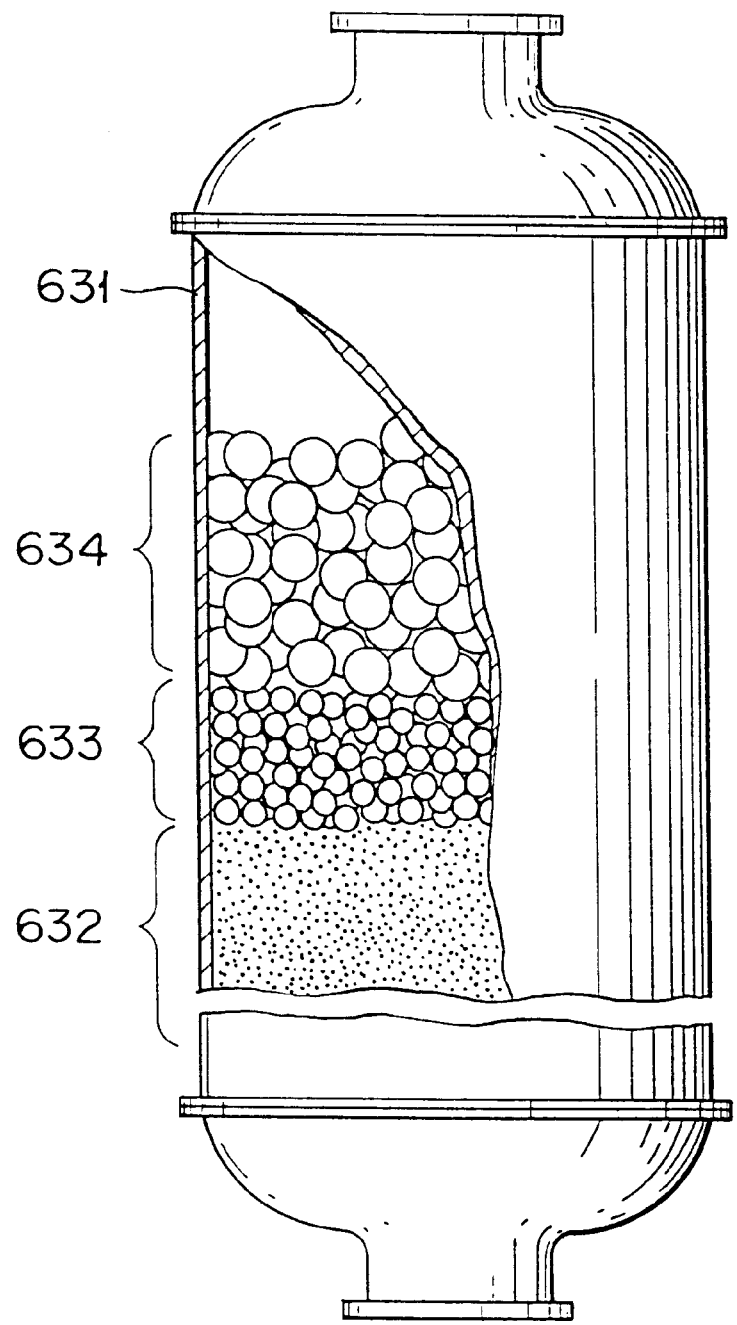
FIG. 6 is an illustration of a catalyst packing, catalyst retaining device in the reactor of Example II-3.

FIG. 6 illustrates the structure of an upper catalyst retainer to be used when the reactor was packed with a catalyst in the up-flow mode. The catalyst to be used for producing an alkanolamine was preferred to have as small a particle diameter as permissible because the diffusion in the catalyst particles posed a problem. The particle diameter of such a catalyst is expected generally to be not more than 1 mm (equivalent diameter where the catalyst particles were not in a spherical shape), preferably in the range of 1–0.1 mm. After the catalyst of such a relatively small particle diameter was packed, a catalyst retainer was used with a view to preventing the catalyst bed from moving or the catalyst particles from flowing out of the reactor. Inert particles were proper for use in the catalyst retainer.

In FIG. 6, the reference numeral 631 denotes a reactor, the reference numeral 632 a catalyst bed, and the reference numeral 633 inert particles of the first layer having a particle diameter of 0.5 to 10 times, specifically 3 times, the particle diameter of the catalyst in the catalyst bed 632. This part was formed of relatively small particles and was capable of repressing the outflow of the catalyst particles. The thickness of this layer is not particularly limited. If it is increased unduly, it will only add to pressure loss without doing any good. Properly, the thickness is 5 to 20 times the diameter of the inert particles.

The shape of the inert particles is not particularly limited. The inert particles in the shape of spheres prove advantageous for the purpose of being packed most closely.

The reference numeral 634 denotes a second layer of inert particles having a particle diameter of 1.5 to 10 times, specifically 5 times, the diameter of the particles of the layer 633. Since this layer is expected to support the first layer, it is preferred to have a relatively large packing density, i.e. 1 g/cm$^3$ to 5 g/cm$^3$.

When the second layer 634 is overlaid by a gap, one or more layers may be further superposed thereon or a demister placed to fill up the gap. The reactor, when necessary, may be provided at the outlet thereof with a filter capable of trapping a fine dust of the catalyst.

Referential Example 1

Preparation of Catalyst

Ten (10) kg of montmorillonite was added with stirring to 500 liters of an aqueous 0. 05 mol/liter yttrium nitrate solution. The resultant mixed liquid was stirred at a room temperature for one day and thereafter filtered. Subsequently, the solid separated by the filtration was washed with 500 liters of purified water. The washed solid and 5 kg of crystalline cellulose powder added thereto were kneaded with a kneader and then extrusion molded into cylinders, 0.4 mm in diameter and 1–3 mm in length. A catalyst was obtained by drying the solid cylinders at 100° C. for one day and treating the dried cylinders at 500° C. for five hours under a stream of air. This catalyst was labeled as "Catalyst A."

Example III-1

Figure 7:
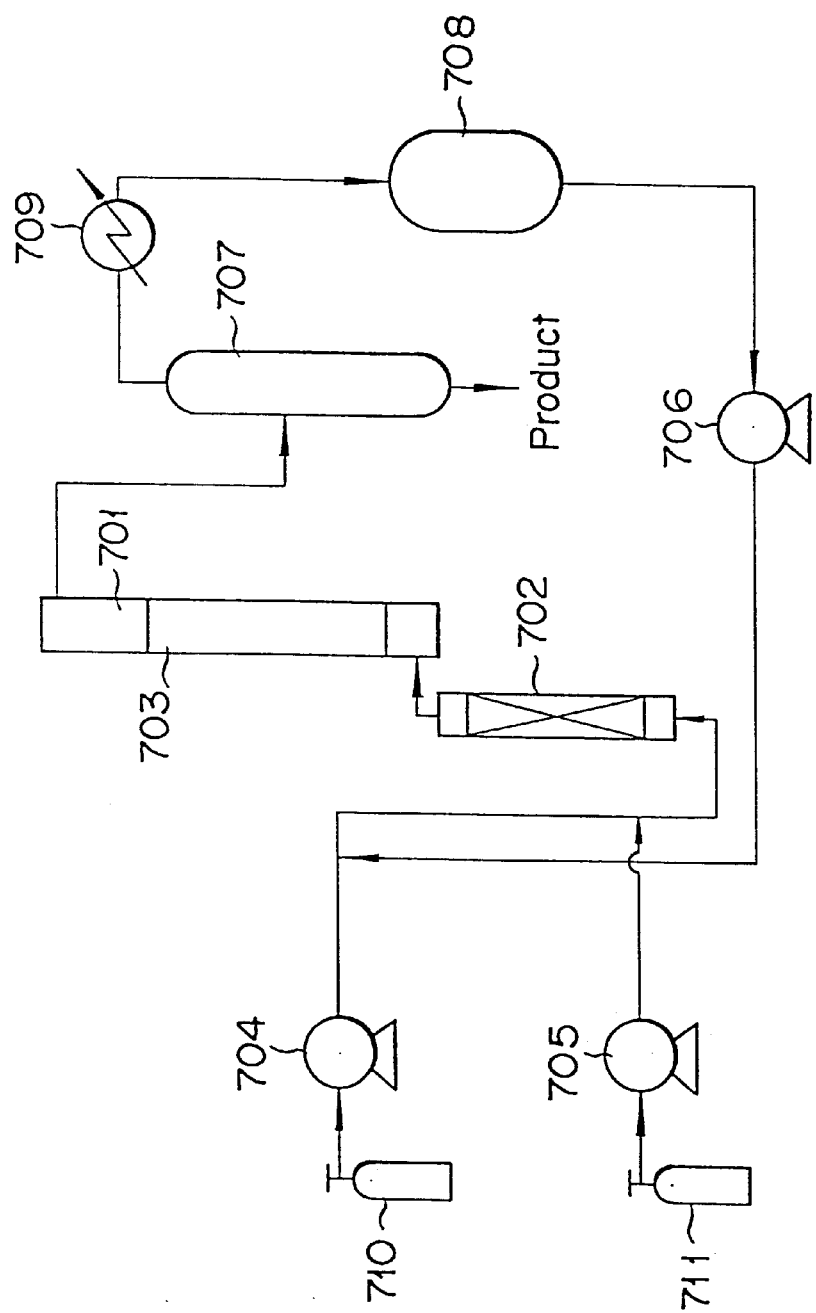
FIG. 7 is a diagram illustrating an apparatus for producing an alkanolamine.

A reaction was carried out in a reaction apparatus shown in FIG. 7 in the presence of Catalyst A. First, a reactor 701 (made of steel and measuring 67 mm in inside diameter) having an inner volume of 7 liters was packed with 6 liters of Catalyst A. In front of the reactor (on the upstream side), a pre-heater 702 (measuring 1 m in length and 5 mm in diameter and including a preheating part, 20 mm in inside diameter) provided on the perimeter thereof with an electric heater (not shown) was disposed. The preheating part was heated by the electric heater. Then, to the pre-heater 702, ammonia and ethylene oxide were continuously fed at stated speeds using high-pressure pumps 704 and 705. As a result, the ammonia from an ammonia cylinder 710 and the ethylene oxide from an ethylene oxide cylinder 711 were mixed and heated and were then supplied to the reactor 701. The reactor 701 was kept in a substantially adiabatic state by being slightly heated by a heater (not shown) and consequently allowed to replenish the quantity of heat lost by radiation. The reaction pressure was controlled to 12 MPa. Then, the ethylene oxide and the ammonia were continuously reacted. As regards the reaction conditions in the steady state, the temperature at the inlet of the reactor was at 55° C., the LHSV at 3.5 $hr^{-1}$, and the ammonia/ethylene oxide molar ratio at 14.

The startup operation for initiating the reaction was carried out by the following procedure, (1)–(5).

(1) The reactor with the temperature thereof at the inlet kept at 100° C. was supplied exclusively with ammonia and then heated till the temperature thereof substantially reached 100° C. as far as the outlet layer.

(2) The supply of raw materials was initiated so as to set the molar ratio of ammonia to ethylene oxide at 25 and the LHSV at 5.25 $hr^{-1}$. The reaction was continued under these conditions for 17 minutes.

(3) The amount of ethylene oxide was increased till the molar ratio of ammonia to ethylene oxide reached 20 and, at the same time, the temperature of the pre-heater was gradually lowered till the inlet temperature fell to 70° C. in 34 minutes.

(4) The amount of ethylene oxide was increased with the LHSV set at 3.5 $hr^{-1}$ till the molar ratio of ammonia to ethylene oxide reached 16 and, at the same time, the temperature of the pre-heater was gradually lowered till the inlet temperature reached 55° C. in 50 minutes.

(5) Subsequently, the static operation was continued, with the molar ratio of ammonia to ethylene oxide set at the prescribed level of 14 and the temperature of the inlet of the reactor set at the prescribed level of 55° C.

Figure 8:
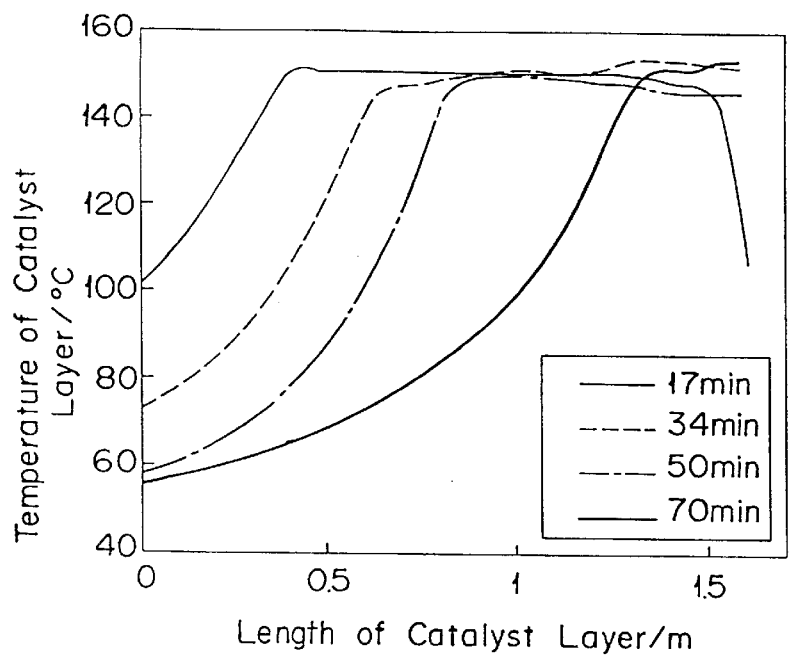
FIG. 8 is a diagram showing the temperature distribution in the catalyst bed of Example III-1.

The temperature distribution in the catalyst bed along the course of time obtained in Example III-1 is shown in FIG. 8. It is noted from the diagram that the temperature of the catalyst bed was wholly kept at a sufficiently high level and showed no sign of abnormal rise. From the initial stage of the start-up, the reaction mixture at the outlet. showed no discernible sign of ethylene oxide, indicating the substantial absence of unaltered ethylene oxide.

Comparative Example III-1

A procedure was carried out by following the procedure of Example III-1 while changing the procedure of startup, namely setting the reaction conditions from the beginning at the prescribed levels (the inlet temperature at 55° C., the molar ratio of ammonia to ethylene oxide at 14, the LHSV at 3.5 $hr^{-1}$, and the reaction pressure at 12 MPa).

Figure 9:
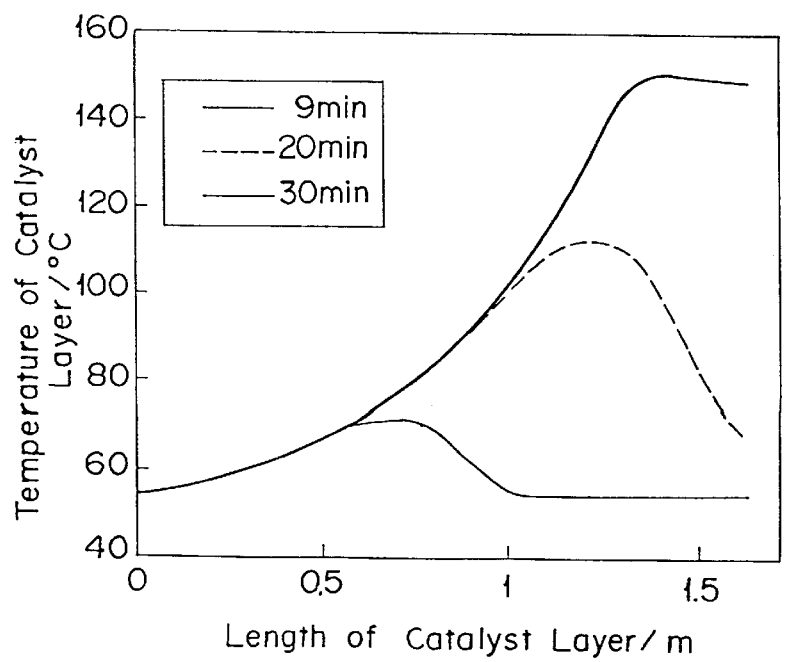
FIG. 9 is a diagram showing the temperature distribution in the catalyst bed of Comparative Example III-11.

FIG. 9 illustrates the temperature distribution in the catalyst layer along the course of time. It is noted from this diagram that the temperature of the catalyst bed was not raised fully satisfactorily during the initial stage and the temperature of the reactor barely began to rise after the elapse of not less than 30 minutes. The degree of conversion of the ethylene oxide during the initial state was only about 40%, indicating that the unaltered ethylene oxide of a large amount flowed out of the reactor.

Example III-2

A static reaction was carried out by following the procedure of Example III-1 while setting the prescribed inlet temperature at 45° C., the molar ratio of ammonia to ethylene oxide at 8, the reaction pressure at 10 MPa, and the LHSV at 3.5 $hr^{-1}$. The startup for initiating this reaction was effected by the following procedure, (1)–(6).

(1) The reactor having the inlet temperature thereof set at 90° C. was supplied exclusively with ammonia and then heated till the temperature thereof substantially reached 90° C. as far as the outlet layer.

(2) The supply of raw materials was initiated so as to set the molar ratio of ammonia to ethylene oxide at 20 and the LHSV at 7 $hr^{-1}$. The reaction was continued under these conditions for 17 minutes.

(3) The amount of ethylene oxide was increased till the molar ratio of ammonia to ethylene oxide reached 18 and, at the same time, the temperature of the pre-heater was gradually lowered till the inlet temperature fell to 60° C. in 34 minutes.

(4) The amount of ethylene oxide was increased with the LHSV set at 3.5 $hr^{-1}$ till the molar ratio of ammonia to ethylene oxide reached 13 and, at the same time, the temperature of the pre-heater was gradually lowered till the inlet temperature reached 45° C. in 50 minutes.

(5) The amount of ethylene oxide was increased till the molar ratio of ammonia to ethylene oxide reached 10 and the reaction was continued for 68 minutes.

(6) Subsequently, the static operation was continued, with the molar ratio of ammonia to ethylene oxide set at the prescribed level of 8 and the temperature of the inlet of the reactor set at the prescribed level of 45° C.

Figure 10:
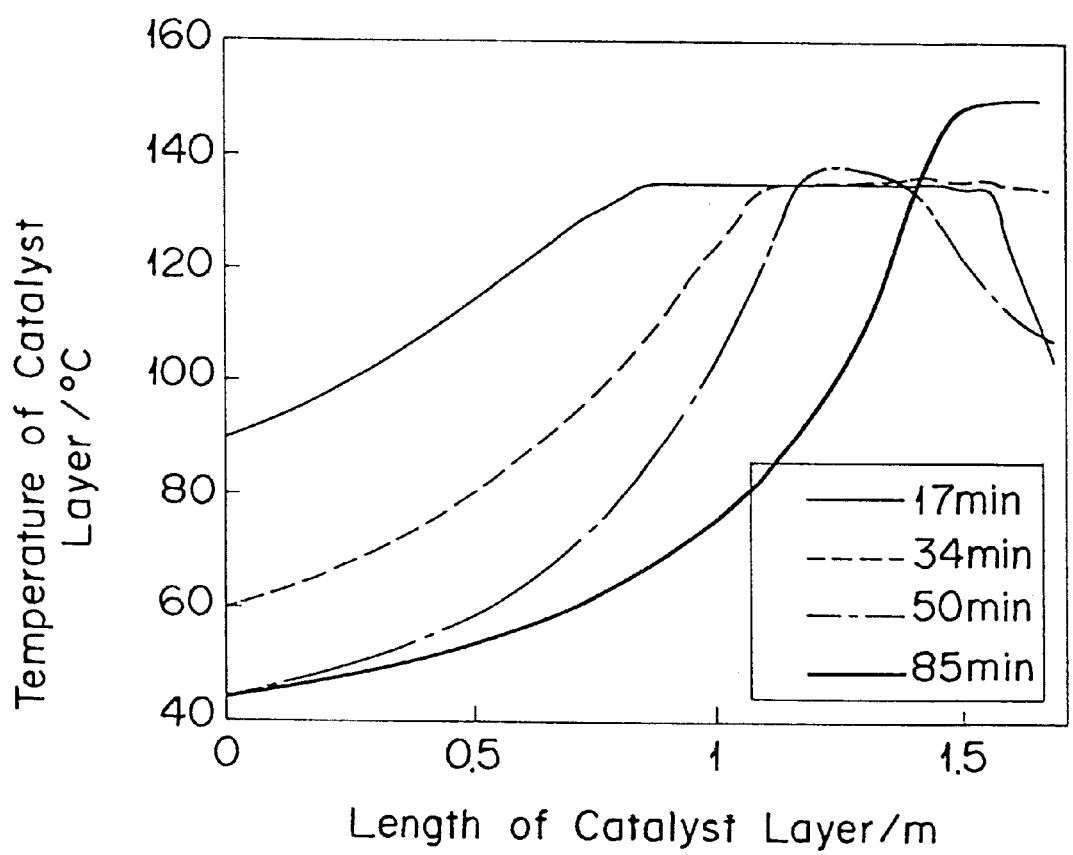
FIG. 10 is a diagram showing the temperature distribution in the catalyst bed of Example III-2.

FIG. 10 illustrates the temperature distribution in the catalyst bed along the course of time. It is noted from this diagram that the temperature of the catalyst bed was maintained wholly at a high level and showed no sign of abnormal rise. From the initial stage of the start-up, the reaction mixture at the outlet showed no discernible sign of ethylene oxide, indicating the substantial absence of unaltered ethylene oxide. It is also noted that the start-up was stably effected even when the molar ratio was as small as 8 and the ethylene oxide concentration high.

Comparative Example III-2

A procedure was carried out by following the procedure of Example III-2 while changing the procedure of start-up from that of Example III-2, namely setting the reactions conditions from the beginning at the prescribed levels (the inlet temperature at 45° C., the molar ratio of ammonia to ethylene oxide at 8, the LHSV at 3.5 hr$^{-1}$, and the reaction pressure at 10 MPa). The temperature of the catalyst bed was not raised fully satisfactorily during the initial stage and the temperature of the reactor barely began to rise after the elapse of not less than 40 minutes. The degree of conversion of the ethylene oxide during the initial state was only about 20%, indicating that the unaltered ethylene oxide of a large amount flowed out of the reactor.

The entire disclosure of Japanese Patent Application Nos. 11-102975, 11-104582 and 11-163920 filed on April 9, 1999, Apr. 12, 1999 and Jun. 10, 1999, respectively, including specification, claims, drawings and summary are incorporated herein by reference in its entirety.

What is claimed is:

1. A reaction apparatus for producing a dialkanolamine by causing an alkylene oxide to react with ammonia and a monoalkanolamine, comprising:

a first mixer connected both to a source of ammonia and to a source of a monoalkanolamine for mixing ammonia with the monoalkanolamine to form a fluid;

a pre-heater, connected to the first mixer, for heating the fluid flowing from the mixer;

a second mixer connected to the pre-heater, having a feed inlet for supplying an alkylene oxide, for mixing the alkylene oxide with the heated fluid flowing from the pre-heater; and a reactor connected to the second mixer for receiving the mixture of the heated fluid and the alkylene oxide flowing from the second mixer for reaction therein, wherein the reactor is equipped with a catalyst bed packed with a solid catalyst.

2. An apparatus according to claim 1, wherein an available volume from the feed inlet for supplying the alkylene oxide through an inlet of the catalyst bed is in the range of 0.01 to 0.5 times the volume of the catalyst bed in the reactor.

3. An apparatus according to claim 1 further comprising a liquid-pervious inert material set on the upstream side in the interior of the reactor.

* * * * *